United States Patent [19]
da la Torre

[11] Patent Number: 5,516,526
[45] Date of Patent: May 14, 1996

[54] COMPOSITIONS CONTAINING DMSO AND FRUCTOSE 1,6-DIPHOSPHATE

[76] Inventor: Jack da la Torre, 10301 Camino del Oso NE., Albuquerque, N.M. 87111

[21] Appl. No.: 408,840

[22] Filed: Mar. 22, 1995

Related U.S. Application Data

[63] Continuation-in-part of Ser. No. 99,357, Jul. 30, 1993, abandoned.
[51] Int. Cl.$^6$ ............... A61F 2/02; A61K 9/70; A61K 31/70
[52] U.S. Cl. ............ 424/449; 424/423; 424/436; 424/DIG. 15; 514/23; 514/25; 514/936; 514/946; 514/947
[58] Field of Search ............ 424/423, 436, 424/449, DIG. 15; 514/23, 25, 936, 946, 947

[56] References Cited

FOREIGN PATENT DOCUMENTS 9503753  2/1995  WIPO .

*Primary Examiner*—Carlos Azpuru
*Attorney, Agent, or Firm*—Glenna Hendericks; Stephen Gates

[57] ABSTRACT

This invention relates to a method of protection from and treatment of neurological damage in mammals by administration of dimethylsulfoxide (DMSO) in combination with fructose 1,6-diphosphate (FDP). The effects of administration of the drugs together, either as two separate compositions or in combination, results in synergistic action that greatly improves protection from morbidity in animals (including humans) who have suffered injury to the brain.

11 Claims, No Drawings

COMPOSITIONS CONTAINING DMSO AND FRUCTOSE 1,6-DIPHOSPHATE

This application is a continuation-in-part of prior application Ser. No. 08/099,357 filed Jul. 30, 1993, now abandoned.

FIELD OF THE INVENTION

This invention relates to a method of protection from and treatment of neurological damage in mammals by administration of dimethylsulfoxide (DMSO) in combination with fructose 1,6diphosphate (FDP).

BACKGROUND OF THE INVENTION

Hypoxemia, ischemia and increased intracranial pressure are associated with many assaults on the brain, including severe head injury, thrombosis, and cerebral hemorrhage. Since the brain has limited reserves of high energy adenyl nucleotides, any condition that results in cerebral ischemia or hypoxia can impair aerobic oxidative metabolism and development of anaerobic glycolysis. Head injury or severe hypoxia can also lead to production of injurious amounts of lactic acid. Moreover, phosphofructokinase (PFK), the rate-limiting enzyme responsible for the conversion of fructose-6 phosphate to fructose 1,6-diphosphate (FDP), can be inhibited during anaerobic glycolysis due to the development of cellular acidosis. The resulting condition is one of rapid decline of intracellular adenosine triphosphate (ATP), the major source of cellular energy. Deterioration of the cerebral energy state can also result in the loss of intracellular $K^+$ while promoting intracellular free $Ca^{2+}$ during depolarization of the neuronal membrane. Experimental evidence has implicated intracellular $Ca^{2+}$ accumulation to a chain of biochemical events leading to irreversible neuronal death. Those events include the uncoupling of oxidative phosphorylation, activation of intracellular enzymes and generation of cell-damaging hydroxyl or oxygen free radicals.

Previous experimental studies have shown that intravenous FDP can improve electrical brain activity and protect cerebral neurons from damage following ischemic injury in rabbits. A number of studies indicate that FDP is useful in improving brain metabolism following ischemia and hypoglycemic coma, ostensibly by increasing intracellular ATP levels and preventing intracellular $Ca^{2+}$ accumulation. FDP appears useful in cardiogenic shock, intestinal ischemia, myocardial infarction or ischemia, renal ischemia, hypoglycemic coma, acute respiratory distress syndrome, liver ischemia and injury, hemorrhagic shock, peritonitis, cardiomyopathy, cardiac arrhythmias and doxorubicin-induced cardiotoxicity. FDP reduced endotoxin shock by preventing intestinal fluid loss, restoring mean arterial pressure and preserving urinary output. One study, however, failed to confirm a benefit by FDP in myocardial ischemia. In many of the studies a consensus opinion is that FDP appears as an ideal agent to increase energy production during anaerobic glycolysis and to reduce the formation of oxygen radicals. Although FDP is a phosphorylated sugar, it crosses the blood-brain barrier and enters the neurons. Theoretically, one mole of FDP yields four moles of ATP whereas one mole of glucose yields only two moles of ATP. In order to produce usable energy from FDP, large quantities of the compound must be administered. FDP has also been shown beneficial in patients with traumatic shock following spinal cord injury, gun-shot wounds to the neck, chest and abdomen, head injury, and duodenal rupture.

The use of dimethyl sulfoxide (DMSO) following cerebral trauma or ischemia is reported to protect cell membranes, increase cerebral blood flow, reduce hydroxyl radical formation, inhibit platelet aggregation and significantly lower elevated intracranial pressure. In monkeys, DMSO has also been shown to be effective after high missile brain injury by improving mean arterial pressure, cerebral perfusion pressure, and cerebral metabolic rate of oxygen. Furthermore, DMSO reduces the cerebral metabolic rate of lactate. The metabolism of lactate can lead to lactic acidosis and eventual impairment of oxidative phosphorylation with decreased production of ATP. For these reasons, use of DMSO to protect brain tissue after vascular and physical insults has been suggested.

DMSO has been shown in numerous experimental studies to reduce intracranial pressure elevation, inhibit platelet aggregation, reduce edema after focal brain ischemia, increase survival after stroke and gun-shot wound to the head. Additionally, it has been reported that DMSO can protect glial cells against sonic damage, increase cerebral and spinal cord blood flow following trauma or ischemia, protect tissue from radiation and cold-induced damage, prevent ischemic damage to the kidney, intestines and brain, improve neurologic outcome after spinal and head trauma and inhibit platelet aggregation in obstructed coronary vessels. Clinical studies have shown that DMSO can improve end-stage acute respiratory distress syndrome and, when given to patients intravenously, can reduce intracranial pressure following severe closed head injury, increase cerebral blood flow following cerebral hemorrhage, reduce amyloid deposition in patients with primary amyloidosis, and improve mitochondrial function and energy metabolism partly due to DMSO's action as a free radical scavenger. DMSO has been shown useful in the treatment of reflex sympathetic dystrophy secondary to inflammatory reactions. DMSO is reported to have important biological activity in reducing conduction of painful stimuli through C-fibers and may have anti-carcinogenic, anti-viral action.

No previous suggestion has been seen that use of dimethylsulfoxide with fructose 1,6-diphosphate would be advantageous. It was not previously known that DMSO and FDP would act synergistically in preventing damage to neuronal tissue.

SUMMARY OF THE INVENTION

It is the purpose of this invention to provide a means of preventing depletion of ATP in the brain during hypoxia and/or ischemia by administering a combination of dimethyl sulfoxide and fructose 1,6-diphosphate in order to deliver to the brain adequate amounts of the substrate required for ATP formation and to thereby prevent the harmful biochemical cascade that results from impaired energy metabolism.

It is a further purpose of the invention to provide compositions of matter which may conveniently be used in treatment of hypoxia/ischemia, including hypoxia/ischemia arising from trauma.

DETAILED DESCRIPTION OF THE INVENTION

It has now been found that using a combination of dimethyl sulfoxide (DMSO) with fructose 1,6-diphosphate (FDP) results in unexpected increase in benefit to patients suffering from cerebral hypoxia/ischemia. The effects of administration of the drugs together, either as two separate compositions or in combination, results in synergistic action that greatly improves protection from morbidity in animals (including humans) who have suffered injury to the brain. The use of DMSO:FDP to protect organ tissue and provide a source of energy for the nerve tissue during energy crisis precipitated by hypoxia, ischemia or tissue edema provides a means of preventing long-term neuronal damage which can result in long-term disability or in death.

MATERIALS AND METHODS

Unanesthetized male CD-1 mice weighing 22-29 grams were restrained and subjected to 800 or 900 gram/centimeter force injury using a special trauma apparatus. Trauma was induced by allowing a thin lead pipe free-fall through a glass tubing for a determined distance to strike the head of the mouse which was carefully positioned under the glass tubing. This injury resulted in immediate loss of consciousness followed by seizure activity lasting 1–2 minutes. Three end-points were measured:

1) ability of compounds to protect from sensorimotor deficits;
2) ability of compounds to reduce mortality; and
3) ability of compounds to reduce neuronal damage from head trauma.

In the first study, mice were randomized into 4 groups of 6 mice per group. There was administered (into the tail vein) one of the following:

DMSO group: 1 g/Kg dimethyl sulfoxide as a 28% solution in 5% dextrose (D5W)

FDP group: 350 mg/Kg fructose 1,6-diphosphate as a 10% solution in D5W

D5W group: D5W alone as a control

DMSO: FDP group: 350 mg/Kg FDP in D5W to which had been added 1 g/Kg of a 28% solution of DMSO. All compounds were injected intravenously 5 minutes following injury and injected volumes ranged between 0.08 ml and 0.07 ml, varying according to each animal's weight. Following an 800 gram/centimeter force injury, mice were placed in a heated cage to maintain body temperature. The trisodium salt of the FDP was used (Sigma, grade 98–100% of FDP with a molecular weight of 406.1 (formula $C_6H_{11}O_{12}P_2Na_3$) was used. DMSO was obtained from Pharma 21 as a pyrogen-free, sterile, 99.9% pharmaceutical grade with a molecular weight of 78.1 (formula $C_2H_6OS$).

FDP is stable at room temperature in its crystalline form, including its salts, for several months and for several days once it is in solution.

The mouse head injury model used in this study is a standard used in pharmaceutical drug testing of potentially useful compounds in severe brain concussive injury.

NEUROLOGICAL EVALUATION

At 1 and 2 hours following head injury, each mouse was tested for sensory deficits by pinching the fore and hind limb toes with a fine forceps. Each mouse was then grasped by the tail and its front or rear paws were allowed to come in contact with a taut string 60 centimeters long suspended between two metal stands 40 cm above a padded table. The tail was then released and the mouse's ability to grasp and hold on to the string for 90 seconds was tested. The length of time each mouse held on to the string (grip test) was then recorded as the latency in seconds and group means were determined at the end of each time point for 1 or 2 hours following the trauma. Each mouse was placed on the string only once for each test period.

RESULTS

The table below shows the "grip test" (time in seconds the mouse held onto the string) for each mouse in each of the four groups tested at 1 and 2 hours following 800 g/centimeter force injury. Values are expressed in seconds.

| GROUP | GRIP TEST: 1 HOUR | GRIP TEST: 2 HOURS |
|---|---|---|
| DMSO | 7 | 3 |
| DMSO | 18 | 15 |
| DMSO | 3 | 4 |
| DMSO | 8 | 5 |
| DMSO | 30 | 60 |
| DMSO | 10 | 14 |
| MEAN | 12.6 | 16.8 |
| FDP | 30 | 27 |
| FDP | 10 | 12 |
| FDP | 2 | 1 |
| FDP | 2 | 2 |
| FDP | 4 | 24 |
| FDP | 16 | 22 |
| MEAN | 10.6 | 14.6 |
| DMSO:FDP | 72 | 84 |
| DMSO:FDP | 60 | 76 |
| DMSO:FDP | 90 | 90 |
| DMSO:FDP | 90 | 90 |
| DMSO:FDP | 90 | 86 |
| DMSO:FDP | 56 | 90 |
| MEAN | 76.3 | 86.5 |
| D5W | 4 | 2 |
| D5W | 17 | 15 |
| D5W | 2 | 12 |
| D5W | 4 | 36 |
| D5W | 7 | 9 |
| D5W | 2 | 1 |
| MEAN | 6.6 | 12.5 |

An additional test was utilized to measure the relative strength of the fore and hind paws on the string for each mouse. This test involved the mouse traveling from the center of the string to one end of the vertical posts holding the string. The test demonstrates the relative motor strength of all four limbs, since all paws are required to allow the mouse to move 30 centimeters toward the end of the string rather than merely holding on to the string, which requires only fore or hind paws. Only 2 mice, both of whom had received the combination DMSO:FDP solution, performed this test. One mouse was able to reach the end of the string 3 times within the 90 second allotment and the second mouse reached the end of the string 2 times.

A second study was performed using additional mice to evaluate mortality following a more severe injury of 900 g/centimeter force injury. The doses and route of administration were the same as described above. If any mouse survived this impact force, they were given a grip test to measure sensorimotor ability. The following results were obtained:

| GROUP | SURVIVED | GRIP TEST: 1 HOUR |
|---|---|---|
| DMSO:FDP | YES | 25 |
| DMSO:FDP | YES | 28 |
| DMSO:FDP | YES | 22 |
| DMSO:FDP | YES | 31 |
| DMSO:FDP | YES | 24 |
| FDP | NO | |
| FDP | NO | |
| FDP | YES | 2 |
| DMSO | YES | 6 |
| DMSO | NO | |
| DMSO | NO | |
| D5W | NO | |

-continued

| GROUP | SURVIVED | GRIP TEST: 1 HOUR |
|---|---|---|
| D5W | NO | |
| D5W | NO | |

All of the mice were killed by decapitation 3 hours after the initial head injury and the brains were processed for Palmgren silver impregnation stain. Four micron sections were taken every 100 μm beginning at the center of the lesion site and proceeding in an antero-posterior direction to the site of trauma. To evaluate neuronal damage, CA1 hippocampal region and fronto-parietal cortex were used for morphometry. The hippocampal region was chosen for morphometry even though it was not directly below the site of trauma because this region is highly vulnerable to brain ischemia and to cerebral swelling following trauma and also because the hippocampus has been linked to learning and memory, functions which are often affected after severe brain trauma. Frontoparietal cortical neurons were evaluated because of their proximity to the lesion site and because damage to this region was relatively consistent among the experimental and non-treated group. Neuronal counts of the fronto-parietal cortex and CA1 region were made by averaging the number of damaged/total neurons from each side of the hippocampus or parietal cortex from five representative sections. Group means were obtained for each treatment and those values were compared to vehicle non-treated controls. Morphometric data was analyzed using a digitizing screen connected to a Jandel program which computed means, sum, standard deviation and standard error. Statistical analyses of group test scores for each time point were made using one-way analysis of variance (ANOVA) with Bonferroni correction by comparing mean grip times of vehicle, non-treated mice for each experimental group treated with single doses of FDP, DMSO or combination FDP:DMSO. A value of $p<0.05$ was considered significant.

The histological findings showed normal shape and arrangement of CA1 and cortical neurons in non-injured control mice and in mice treated with fructose 1,6-diphosphate and DMSO. By contrast, moderate neuronal damage was seen in CA1 and cortex in animals that received either fructose 1,6-diphosphate or DMSO alone. Severe neuronal damage was noted with vehicle, non-treatment where injury extended to the external row of neurons of CA1 and in the cortex where many perineuronal spaces were associated with shrunken, pyknotic neurons.

In view of the above, it is concluded that sensorimotor sparing in the group given DMSO:FDP as compared to the other groups was significantly greater than the use of either DMSO or FDP alone in all instances. It was also concluded, from the morphometric data, that the combination of FDP:DMSO had a protective effect on CA1 hippocampal and frontoparietal cortex neurons where the amount of damage was significantly lower than with FDP or DMSO alone or with animals treated with the vehicle. Statistical analysis shows that these differences are highly significant ($p<0.002$) using analysis of variance (ANOVA) and the non-parametric Mann-Whitney two sample test. The incidence of mortality was also greatly decreased in the mice subjected to severe concussive force to the head. Hence, the evidence indicates that there is unexpected synergistic effect for treatment with DMSO:FDP when compared with use of DMSO alone or FDP alone.

While the model tested for use of the compositions of the invention was a severe mode, the compositions may be used to treat other disease conditions arising on account of ischemia and hypoxia. Such conditions include, in addition to closed head injury, any condition that will cause cerebral ischemia/hypoxia or increase intracranial pressure such as stroke, arachnoidal cysts, neoplasms, hydrocephalus, tuberculous meningitis, meningocele, pseudo-tumor cerebri, lead encephalopathy, gun-shot wounds, acquired immunodeficiency syndrome (AIDS), Reye's syndrome, and meningitis (including bacterial, fungal and vital meningitis.) The compositions may also be used to treat other disease conditions that cause ischemia or hypoxia, including myocardial insufficiency, brain edema, tumors, vascular malformations, hemorrhagic shock, cardiogenic shock, traumatic brain coma, spinal cord injury, spinal tumor, syringomyelia. The compositions of the invention can also be used in treatment of cerebral energy-related disorders including neurodegenerative disorders such as Alzheimer's disease, Parkinson's disease, multiple sclerosis, amyotrophic lateral sclerosis, adrenoleukodystrophy, dementia pugilistica, Huntington's chorea, multiinfarct dementia, Pick's disease, hepatic encephalitis and kernicterus.

Two human patients were treated with fructose 1,6-diphosphate and DMSO.

Patient #1:

The patient was admitted for a severe head injury with brain tissue extruding from the wound. A solution containing 28% DMSO and 10% FDP made with 5% dextrose in water was given in three divided doses to provide a total dosage of 200 mg/Kg/day for 4 days. On the fourth day, the patient opened her eyes and was able to follow commands. She then underwent surgery for her injury.

Patient #2:

The patient was treated for cerebral infarction of the left internal capsule (verified by MRI scan) of 3 months duration using 10% FDP and 28% DMSO solution as described above. Prior to treatment, the patient could not move the fingers of the right hand or raise the partially paralyzed right arm above the horizontal plane. On the third day of treatment, the patient was able to partially move the fingers of the right hand and raise her right arm above her head.

Compositions containing dimethyl sulfoxide and fructose 1,6-diphosphate may be administered parenterally (including intravenously, intramuscularly, intrathecally and subcutaneously),and topically, including to the mucosa or skin, (for example, sublingually and by inhalation) or by mouth. Compositions administered for contact with the mucosa or skin (for example, rectally or sublingually) result in systemic effects. DMSO:FDP compositions may be administered as retention enemas or in the form of suppositories.

Example 1

Preparation of solution containing active agents

A pre-weighted vial of trisodium salt of fructose 1,6-diphosphate is dissolved by agitation in D5W (Dextrose 5% in water) to make up a final solution of 10% FDP. A measured volume of 100% sterile, pyrogen free pharmaceutical grade DMSO is added to the FDP in D5W to make up a final solution of 28% DMSO. The DMSO:FDP mixture in D5W will remain stable for several days at room temperature and for several weeks at 4° C. It is recommended that the DMSO:FDP solution be used soon after its preparation.

Example 2

Patch Preparation

A patch composed of trilaminate of an adhesive matrix sandwiched between a non-permeable backing and a protective covering layer is prepared in the following manner:

To a pressure-sensitive silicone adhesive composition such as BIOPSA™ Q7-2920 (Dow Corning Corp., Midland, Mich., U.S.A.) in DMSO (50% w/v) is added sufficient saturated solution of fructose 1,6-diphosphate in D5W to provide 10 mg fructose 1,6diphosphate per ml. The adhesive is applied to a polyester film in successive layers to provide about 5 mg of FDP cm$^2$. The film containing the adhesive is then made into patches of 10 cm$^2$. Patches would be covered with a protective layer to be removed before application of the patch. (Since DMSO is a permeation enhancer, there is no need to provide other permeation enhancers in making the patches.)

Example 3

Preparation in Ringer's lactate

A pre-weighted vial of the calcium monohydrate salt of fructose 1,6-diphosphate is dissolved by agitation in Ringer's lactate to make up a final solution of 10% FDP. A measured volume of 100% sterile, pyrogen free pharmaceutical grade DMSO is added to the FDP in Ringer's lactate to make up a final solution of 28% DMSO.

Example 4

Preparation of saturated bandage for application to the skin

DMSO is added to an equal amount of a 0.9 sodium chloride in water. Sufficient fructose 1,6-diphosphate in the form of the calcium monohydrate is added to the DMSO/saline solution to provide 10 mg fructose 1,6-diphosphate per ml. Three ml of the resulting fructose/DMSO solution is absorbed onto a small sponge. A dressing is constructed by placing the sponge on the skin of the inner arm, a water-impermiable covering is placed over the sponge, and the entire dressing is affixed to the arm by means of adhesive strips.

Compositions of the invention can also be used for donor organ preservation. It is well known that in the absence of oxygen, ATP breaks down rapidly. After twenty four hours, ATP loss is about 90% from liver, kidney and heart tissue. It is believed that as a consequence of the ATP loss, alteration in the activities of the enzyme systems occurs. Such alteration leads to eventual irreversible organ injury. DMSO protects donor organs prior to transplantation. FDP increases tissue levels of endogenous ATP. These agents in combination produce better viability and preservation of the donor organ.

Example 5

Solution for the protection of donor organs

Fructose 1,6-diphosphate (FDP) is dissolved to make up a final solution of 10% w/v in half normal saline. DMSO is added to make up a composition containing 10% DMSO. (Final concentration of FDP of about 9%)

It is understood that the concentration of both FDP and DMSO may vary considerably so long as the amounts provided are sufficient to protect the organ from injury and to result in maintenance of sufficient levels of ATP to maintain cellular function.

Salts of the fructose 1,6-diphosphate may be used in preparation of the compositions of the invention. Particularly preferred are the acid addition salts including, but not limited to, potassium salts, including the known potassium diphosphate, sodium salts, including the sodium triphosphate, ammonium salts, magnesium and calcium salts. The calcium and magnesium salts may be in the form of the monohydrate. Dosage for administration of DMSO to animals would vary from about 10 mg/Kg to 1500 mg/Kg while dosage of FDP would be about 1 mg/Kg to 600 mg/Kg. The active agents may be administered in any appropriate pharmaceutically acceptable carrier. Isotonic solutions are appropriate, particularly when the composition is administered intravenously. Examples of such carriers are 5% dextrose, Ringer's lactate solution, or normal physiological saline.

For delivery in suppositories, the FDP could be provided as a saturated solution in a suppository form for administration in conjunction with DMSO.

I claim:

1. A neuronal protective composition of matter comprising, in combination, neuronal protective amounts of dimethyl sulfoxide and fructose 1,6-diphosphate or a pharmaceutically acceptable salt thereof in a pharmaceutically acceptable carrier.

2. A composition of claim 1 wherein the neuronally protective amount of fructose 1,6-diphosphate is present in the composition as a salt.

3. A composition of claim 1 containing a neuronally protective amount of from 50 to 1500 mg dimethyl sulfoxide and a neuronally protective amount of from 1 to 600 mg fructose 1,6-diphosphate.

4. A composition of claim 1 containing, in the pharmaceutically acceptable carrier solution, dextrose.

5. A composition of claim 1 wherein the pharmaceutically acceptable carrier is an isotonic solution.

6. A composition of claim 1 which is formulated as a patch.

7. A method of treating neuronal injury by administration of a composition of matter comprising, in combination, neuronal protective amounts of dimethyl sulfoxide and fructose 1,6-diphosphate or a pharmaceutically acceptable salt thereof in a pharmaceutically acceptable carrier.

8. A method of claim 7 wherein the dosage administered contains a neuronally protective amount of from 50 to 1500 mg dimethyl sulfoxide and a neuronally protective amount of from 1 to 600 mg fructose 1,6-diphosphate.

9. A method of claim 7 wherein the dosage is administered as a patch.

10. A method of claim 7 wherein the active agents are delivered rectally.

11. A method of claim 7 wherein the composition is delivered intravenously.

* * * * *